United States Patent [19]

Prokhorov et al.

[11] 4,164,222

[45] Aug. 14, 1979

[54] LASER OPHTHALMOLOGICAL UNIT

[75] Inventors: Alexandr M. Prokhorov; Alexandr L. Vinogradov, both of Moscow; Jury K. Danileiko, Troitsk Moskovskoi oblasti Podolskogo raiona; Alexandr A. Manenkov, Moscow; Mikhail M. Krasnov, Moscow; Leonid P. Naumidi, Moscow, all of U.S.S.R.

[73] Assignees: Fizichesky Institut Imeni P.N. Lebedeva Akademii Nauk SSSU of USSR; Vsesojuzny Nauchno-Issledovatelsky Institut Glaznykh Boleznei, both of Moscow, U.S.S.R.

[21] Appl. No.: 813,278

[22] Filed: Jul. 6, 1977

[30] Foreign Application Priority Data

Jul. 12, 1976 [SU] U.S.S.R. .............................. 2373635

[51] Int. Cl.$^2$ ............................................ A61B 17/36
[52] U.S. Cl. ................................................ 128/303.1
[58] Field of Search ........................... 128/303.1, 395; 331/94.5

[56] References Cited

U.S. PATENT DOCUMENTS

| 3,653,384 | 4/1972 | Swope | 128/303.1 |
| 3,703,176 | 11/1972 | Vassilladis et al. | 128/395 |
| 3,720,213 | 3/1973 | Hobart et al. | 128/395 |
| 3,828,788 | 8/1974 | Krasnov et al. | 128/303.1 |
| 3,910,276 | 10/1975 | Polanyi et al. | 128/303.1 |
| 4,069,823 | 1/1978 | Isakov et al. | 128/303.1 |

Primary Examiner—Lawrence W. Trapp
Attorney, Agent, or Firm—Steinberg & Blake

[57] ABSTRACT

A laser ophthalmological unit comprises a lasing source and an optical system having a slit source for illumination of the surgery field. This laser and illumination source are housed in a common casing hinged on the bracket of the microscope designed for observation of the surgery field. The emission supply system of said slit source and of the laser are mounted rigidly on said hinged casing but can be adjusted.

5 Claims, 1 Drawing Figure

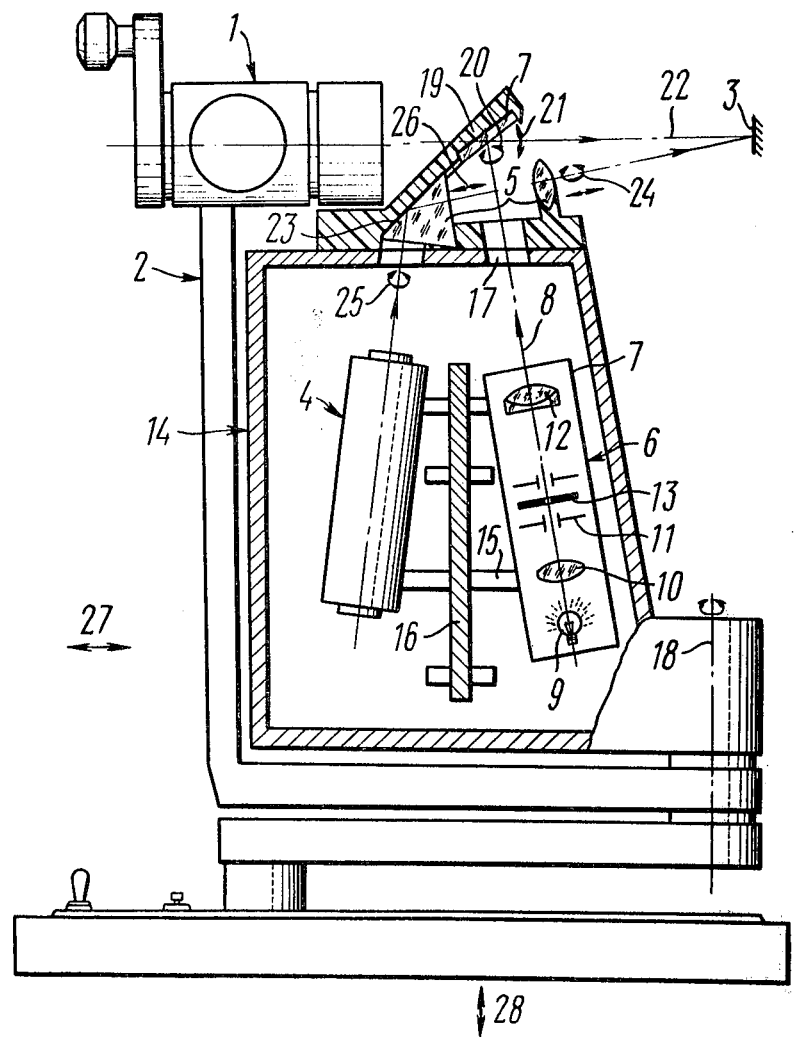

LASER OPHTHALMOLOGICAL UNIT

The present invention relates to medical equipment and, in particular, to apparatuses for treatment of eye diseases, namely to laser ophthalmological units, and can be successfully employed for treatment of glaucoma, cataract and some other diseases of organs of vision.

BACKGROUND OF THE INVENTION

Units whose biological effect is based upon laser emission have lately found wide application in ophthalmologa. They ensure bloodless, contactless, microscopically accurate and strictly measured effect on tissues and medium of the eye globe which does not require any anesthesia.

At present two main, though basically different approaches to the use of laser ophthalmological units for treatment of eye diseases have taken shape. The first approach is connected with laser coagulation of various tissues and mediums of the eye globe. Laser ophthalmological units designed for such purposes are referred to as laser ophthalmocoagulators and their lasing sources are continuous wave lasers (vast majority are argon or krypton lasers; cf., for example, U.S. Pat. No. 3,720,130 filed Mar. 13, 1973) or pulsed free-running lasers (cf., for example, U.S.S.R. Author's Certificate No. 937,318/25-25 filed Jan. 8, 1965).

The clinical effect in such apparatuses is achieved through the thermal action of said lasers leading to coagulation of the tissue.

The second approach to the use of laser ophthalmological units is fundamentally different from the first one and is connected with the use of the laser beam for making holes, tearing of various portions of eye tissues etc. This is achieved through the use of Q-switching of the laser emission (so called giant pulse operation). The action of such laser emission cannot be defined by the term "coagulation" or "cauterization," since it is based on non-thermal effects of the laser beam caused by the great power of the laser pulse. Laser ophthalmological units of the second type are at present employed mainly for treatment of glaucoma (cf., for example, U.S. Pat. No. 3,884,236 filed May 20, 1975 by M. M. Krasnov under the title "Method of Treatment of Glaucoma by Laser").

Any laser ophthalmological unit comprises the following basic components: the laser proper, whose emission is directed to the part of the patient's eye to be treated; a slit illumination system for lighting and selecting the surgery field in the process of accurate steering of the laser beam to the preselected part of the patient's eye; a microscope for watching the surgery field and the position of the marker indicating the focus point of the laser beam; a laser emission supply and focusing system; lighting system providing a marker to steer the laser beam to the preselected part of the patient's eye.

Thus, for example, there is known a laser ophthalmological unit for treatment of glaucoma described in the U.S. Pat. No. 3,828,788 authored by M. M. Krasnov and others. This unit, apart from the above enumerated components of the lighting system, comprises an additional He-Ne laser which produces a marker on the surgery field and a special optical element to match the beam of this laser with the operating beam. Both lasers are rigidly connected and are a single unit mounted upon its own foundation, whereas the slit source of illumination is arranged separately and its beam is directed at an angle to the optical axis of the laser beam. The optical system for supply of the laser emission to the surgery field is rigidly connected to the optical microscopic observation system by attaching the focusing element directly to the casing of the microscope.

One of the main drawbacks of the above described unit consists in that the focusing element is rigidly attached to the casing of the microscope and is, therefore, located in front of the microscope lens. Such attachment, on the one hand, makes it impossible to move the slit illuminator in the opposite position with respect to the vertical plane of symmetry and this is evidently inconvenient for the operator when he is working in different peripheral portions of the eye globe and, in particular, when operating on both of the patient's eyes. Besides, the same reason makes impossible slit illumination along the observation axis which is a necessity in some clinical cases. On the other hand, rigid connection of the focusing element and the microscope lens make it impossible for the operator to direct the laser beam at different angles to the optical observation axis, which sometimes prevents efficient use of the unit when laser action is to be accompanied by observation in the optical section.

Another drawback of such a unit consists in the presence of a second laser, since it significantly complicates the design of the unit and increases its cost. Besides, the division of the laser unit and the slit source, as well as the necessity to converge two laser beams result in inevitable lengthening of the optical path of the operating laser beam, widening of its aperture due to divergence, increased aberrations of the optical system and, consequently, optical losses and wider local diameter of the laser beam.

SUMMARY OF THE INVENTION

It is an object of this invention to provide a laser ophthalmological unit ensuring complete freedom of all degrees of freedom of manipulation by the microscopic device, the operating laser beam and the slit lighting source.

Another object of the present invention is to increase the efficiency of the laser action by shortening of the optical path of the operating laser beam and, consequently, reduction of laser emission losses and greater power of emission in the focusing point.

Still another object of the invention is to eliminate the additional laser lighting source in the system of laser beam guidance to the surgery field.

Finally, it is an object of this invention to simplify the design of the laser ophthalmological unit as a whole.

These and other objects are achieved in a laser opthalmological unit comprising a lasing source provided with a system supplying laser emission to the surgery field, a lighting system for guiding the laser beam to the object, an optical system for illuminating the surgery field and system of microscopic observation, according to the invention, the lasing source and the surgery field illumination optical system featuring a light-transmitting element with a marker for guiding the laser beam to the object are rigidly secured together and housed in a casing hinged so that it can rotate around an axis common with the microscope, the optical elements of the system for supplying the laser emission to the surgery field being installed outside the casing and rigidly connected thereto.

The advantages of such a device consists in that rigid attachment of all components of the emission unit in a casing hinged on the microscope bracket permits preservation of complete freedom of manipulation for the ophthalmologist turning the operating laser beam with respect to the microscopic observation device and, besides, permits the use of a system for supplying the laser emission to the surgery field, which comprises a minimum number of optical elements—a turning element and a focusing element, which reduces losses of laser emission on the way through the optical path due to lesser number of reflecting surfaces and reduces aberrations of the focusing element. The slit source system is combined with the light-transmitting element featuring a marker and this makes it possible to abandon the additional source for producing the marker on the object and to use one white light source both for the slit lighting of the object and for guidance of the operating laser beam.

In order to obtain the marker, it is advisable to provide in the surgery field slit illumination system a light-transmitting element with a marker whose image on the surgery field indicates the focusing point of the operating laser beam. Such design permits guidance of the laser beam in any point of the surgery field in the most uncomplicated manner. Though the elements of the optical system can be installed in different parts of the ophthalmological unit, it is most advisable that these elements be secured on the casing of the slit illuminator. Such design permits the simplest technical embodiment and minimum dimensions of the operating laser beam source and the surgery field slit illumination source provided with a laser beam guidance system.

BRIEF DESCRIPTION OF THE DRAWINGS

The invention will now be described in greater detail with reference to a specific embodiment thereof, taken in conjunction with the accompanying drawing, wherein:

The FIGURE shows schematically a partial cut-off view of a laser opthalmological unit, according to the invention.

DESCRIPTION OF PREFERRED EMBODIMENT

Referring to the FIGURE, the proposed laser opthalmological unit comprises a microscopic observation device 1 mounted upon a bracket 2 and intended for observation of the patient's surgery field 3, a laser 4 with an optical system 5 ensuring supply and focusing of the laser emission on the surgery field 3, a slit source 6 with a deflecting element 7 for supplying the emission to the surgery field 3. Any of the known microscopes having sufficient magnification can be used as the microscopic observation device.

The laser 4 is any usual Q-switched laser, e.g. a ruby laser.

The slit source 6 is provided with a shell wherein the following components are located along a common optical axis 8: a light source 9 (for example, an iodine incandescent lamp), a lens 10 producing a parallel beam from the source 9, two slit apertures 11 and a lens 12 formed by a double-convex and a plano-concave lenses. In principle the above design of the slit source is widely known and employed in ophthalmology. The slit source proposed here is characterized in that between the slit aprtures there is a neutral light filter 13 with a transmission coefficient of the order of 10%, whose central part has a clear part with a transmission coefficient close to 100% and with a diameter of about 0.2 mm. It should be pointed out that such an optical element featuring a marker can be made by different methods. Thus, it can be a plate with a transmission coefficient close to 100% and the marker is tinted in some colour. There is in the central part of the surgery field 3 a region with a diameter of the order of 0.2 mm, possessing a higher degree of illumination which enables the operator to select a spot and to guide the beam to this spot of laser application.

The laser 4 and the slit source 6 are placed in a casing 14 and rigidly connected together by means of fastenings 15 on a post 16 which is in turn secured rigidly in fixing points on the casing 14. The upper part of the casing 14 is provided with windows 17 to let the beams of the laser 4 and the slit source 6 out of the casing. The casing 14 is hinged on the bracket of the microscope 1 (hinged connection is shown as the dotted line 18) which permits all required degrees of freedom in manipulation of the laser beam and the illumination system with respect to the microscope and the surgery field 3. In this case the axis of the hinge should lie simultaneously in the focal plane of the optical system 5, the microscope 1 and the slit source 6.

A holder 19 is rigidly secured on the wall of the casing 14 and carries said light-deflecting element 7 (in this embodiment—an aluminum mirror) provided with an adjustment mechanism for alignment rotations around (indicated by an arrow 20) and perpendicular to (arrow 21) an axis 8 of the slit source beam. The slit source 6 is installed in the casing 14 so that its optical axis 8 is directed to the central part of the deflecting element 7 and after reflection is in one plane with an optical axis 22 of the microscope 1. The same holder 19 carries elements 23 and 24 of the optical system 5 for supply and focusing of laser emission on the surgery field 3. In this case the turning element 23 is provided with an adjustment mechanism for shifting it around (25) and along (26) the laser beam axis. In order to increase the resistance of the turning element to intense laser emission, it is made as a prism having respective angles of the reflecting surface selected so that the incident and outcoming beams are perpendicular to the prism faces in order to minimize losses of laser emission.

It should be noted that the laser 4 and the slit illumination system are arranged within the casing 14 so that their optical axes lie in one plane and constitute an angle from 0° to 15°. The restriction of the angle between the optical axes of said elements is accounted for by the fact that, if the indicated range is exceeded, the dimensions of the casing 14 inevitably grow.

The proposed unit operates as follows. The unit is at first adjusted by moving the prism 23 along the axis of the lens 24 (direction 26) and turning it perpendicular to said axis so that the axis of the laser beam which has passed through the prism 23 is matched with the axis of the lens 24. Afterwards, by moving the lens 24 along its optical axis the laser beam focusing point is brought into coincidence with the image plane of the slit apertures. The mirror 7 is then shifted as indicated by the arrows 20 and 21 and the laser beam focusing point is brought into coincidence with the image of the marker.

When working with the help of this unit, the ophthalmologist makes the usual microscopic inspection of the patient's eye and selects the object of the laser application by moving the slit illuminator along the directions 27 and 28 by means of devices common for all such units and rotating it about the axis 18. Guidance of the laser beam is performed by bringing the light marker of the lighting system to the selected object of application by said movements in the directions 27, 28 and 18. The object in this case is automatically brought in the focal plane of the microscope lens, which corresponds to the maximum sharpness of the object image and the marker. After the unit has been aimed to the spot of the laser application, the laser is started by means of a button or a foot pedal. The object is subjected to the action of the laser emission of preselected parameters controlled by the ophthalmologist by means of the control unit which is a part of the power supply unit.

It should be pointed out that one of the advantages of this invention consists in the fact that the already existing slit illumination sources are employed here and only slight modifications are needed to obtain the above described system. These modifications consist in introduction of a marker and installation of a slit laser source, which is quite practicable since the casing has more than enough space for that. Fastening of the optical system elements presents no difficulties.

Thus, the use of the proposed unit permits the following:

1. Wider clinical use of the unit. The proposed unit is applicable in all cases where its prototype can be used and, moreover, in some clinical cases where laser action is to be combined with simultaneous observation in the optical section; when a laser beam is to be applied at a great angle to the observation axis; when peripheral parts of the eye globe are to be acted upon. Besides, the use of the proposed optical circuit featuring a minimum number of optical elements in the system for supplying the laser emission to the surgery field permits a significant rise in the power density of laser emission in the focusing zone on the object and smaller diameter of the focussed laser emission spot. The proposed unit can be employed, apart from treatment of glaucoma, for treatment of cataract and some other diseases of the eye, that is in cases when the prototype unit is hard to use due to the insufficiently powerful focused beam producing a rather large-diameter spot of the laser beam.

2. Higher clinical efficiency of the laser action as compared to the prototype owing to better optical circuit of the unit, which ensures smaller spot of the focussed laser beam.

3. Higher reliability of the clinical use of the unit due to the fact that the system ofor supplying the operating laser emission to the surgery field comprises no moving elements in the optical circuit and in the mechanical structure.

What is claimed is:

1. A laser ophthalmological unit comprising a laser producing a powerful light emission in order to exert the action upon the patient's eye; an optical system for supplying and focusing the laser emission to a specified point of the patient's eye; an optical system for illumination of the surgery field, comprising a slit source provided with a light-transmitting element with a marker for guiding the laser beam to a specified point of said patient's eye; an optical deflecting element for directing the slit source beam to the patient's eye; a casing wherein said lasing source and said slit illumination source are housed and rigidly secured together, the optical elements of the system for supplying the powerful laser beam and said deflecting optical element mounted outside said casing are rigidly secured to said casing but can be moved for alignment so that optical axes of both systems can coincide in a specified point where the patient's eye is located; a microscope having an axis of rotation for observation of the surgery field; a hinge securing said casing for rotation around the axis of rotation of the microscope, which lies in the focal plane of both said systems and the microscope, and as a result irrespective of the angle between the optical axes of said microscope and said slit illumination source, the marker is always in the focal plance of said microscope.

2. A laser ophthalmological unit as claimed in claim 1, wherein the casing is hinged on the microscope bracket.

3. A laser ophthalmological unit as claimed in claim 1, wherein in order to guide the operating laser beam to the ophthalmological object a light-transmitting element provided with a marker is used in the surgery field slit illumination system, the image of said marker on the ophthalmological object indicating the focusing point of the operating laser beam.

4. A laser ophthalmological unit as claimed in claim 1, wherein the optical system ofor supplying lasing emission to the surgery field comprises a reflecting element rigidly secured on the casing so that it can be shifted for adjustment in two perpendicular planes and along the axis of the operating laser beam.

5. A laser ophthalmological unit as claimed in claim 1, wherein the axis of the operating laser beam and the optical axis of the slit illumination source lie in one plane and form an angle of from 0° to 15°.

* * * * *